United States Patent [19]

Link

[11] Patent Number: 4,727,884

[45] Date of Patent: Mar. 1, 1988

[54] TECHNIQUE FOR OBTAINING THE MEAN BLOOD PRESSURE CONSTANT FOR AN INDIVIDUAL'S BLOOD PRESSURE

[76] Inventor: William T. Link, 130 The Uplands, Berkeley, Calif. 94705

[21] Appl. No.: 60,666

[22] Filed: Jun. 10, 1987

Related U.S. Application Data

[63] Continuation of Ser. No. 868,252, May 28, 1986, abandoned.

[51] Int. Cl.$^4$ ............................................... A61B 5/02
[52] U.S. Cl. ..................................... 128/681; 128/677
[58] Field of Search ................. 128/672, 677, 680–683

[56] References Cited

U.S. PATENT DOCUMENTS

| | | |
|---|---|---|
| 3,903,872 | 9/1975 | Link ..................................... 128/681 |
| 4,009,709 | 3/1977 | Link et al. ........................... 128/681 |
| 4,074,711 | 2/1978 | Link et al. ........................... 128/681 |
| 4,154,238 | 5/1979 | Link ..................................... 128/681 |
| 4,174,707 | 11/1979 | Link et al. ........................... 128/681 |
| 4,367,751 | 1/1983 | Link et al. ...................... 128/681 X |
| 4,418,700 | 12/1983 | Warner ........................... 128/672 X |
| 4,564,020 | 1/1986 | Link ..................................... 128/677 |

FOREIGN PATENT DOCUMENTS

| | | |
|---|---|---|
| 8600208 | 1/1986 | PCT Int'l Appl. ................. 128/677 |
| 2092309 | 8/1982 | United Kingdom ................ 128/672 |

OTHER PUBLICATIONS

Yamakoshi et al.; "New Oscillometric Method for Indirect Measurement of Syst. and Mean Arterial Pressure in the Human Finger" Part 1–Model Experiment Med. and Biol. Eng. and Comput., 1982, 20, pp. 307–313 and Part 2–Correlation Study, pp. 314–318.

*Primary Examiner*—William E. Kamm
*Assistant Examiner*—Angela D. Sykes

[57] ABSTRACT

A non-invasive technique for approximating the mean pressure value and blood pressure constant associated with the actual blood pressure in a particular artery of a given subject is disclosed herein. In accordance with this technique, a number of cuff pulses at varying cuff pressures are generated from the actual blood pressure of the subject and the mean value of the cuff pulse having a maximum peak to peak amplitude value is determined. This mean value is utilized as an approximation of the mean value of the patient's actual blood pressure and is also used in combination with the patient's diastolic and systolic blood pressures to provide the approximation of the patient's blood pressure constant.

9 Claims, 7 Drawing Figures

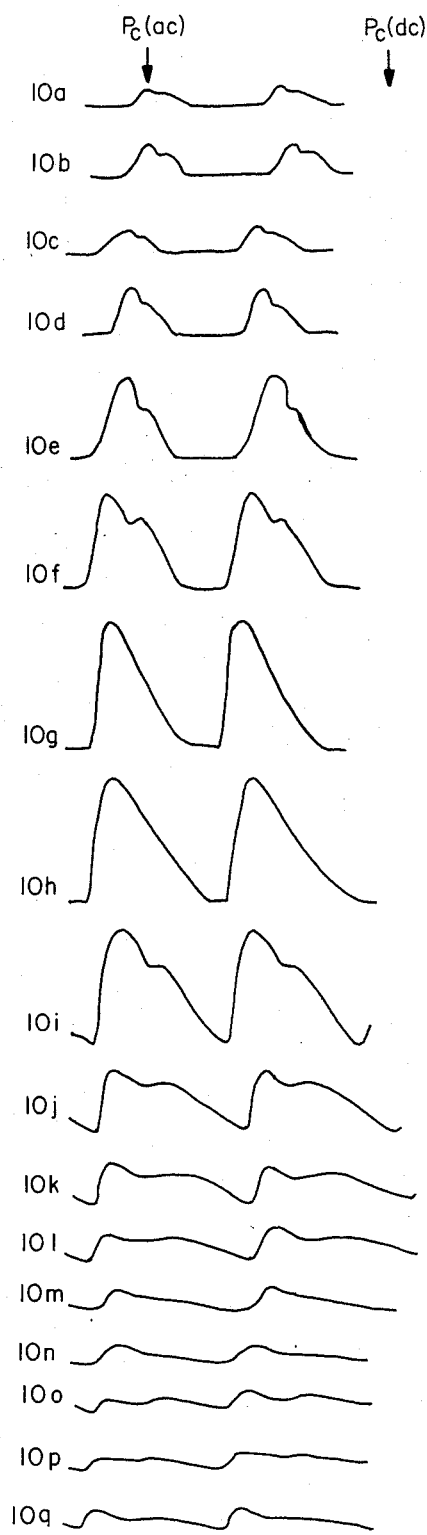
FIG.—1

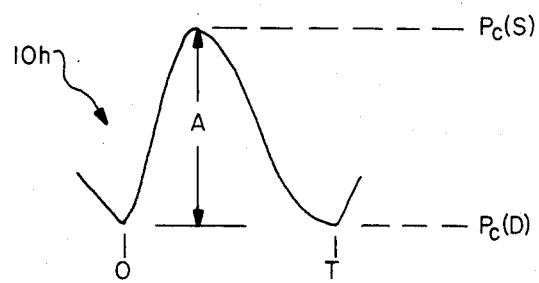
FIG.—2
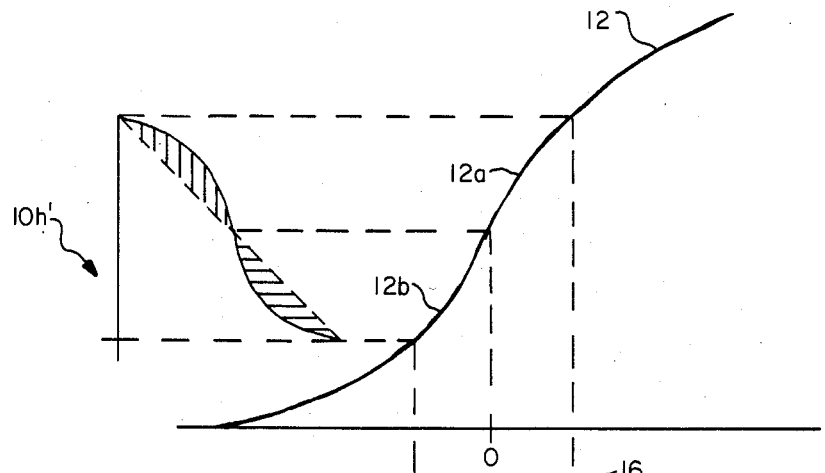
FIG.—3
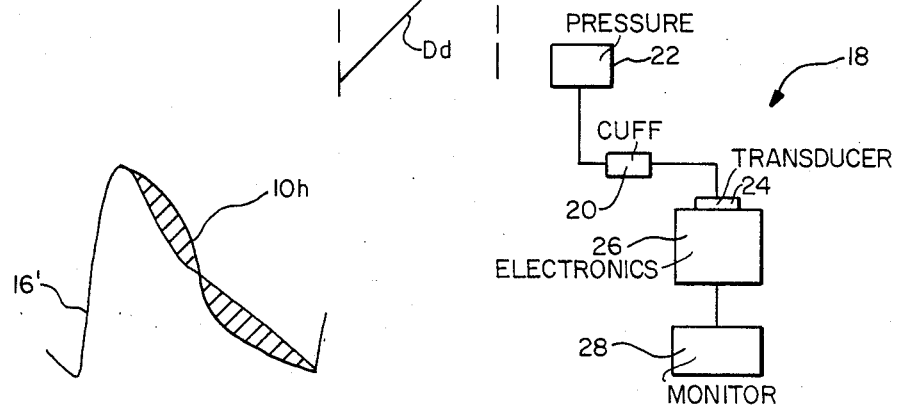
FIG.—4
FIG.—5

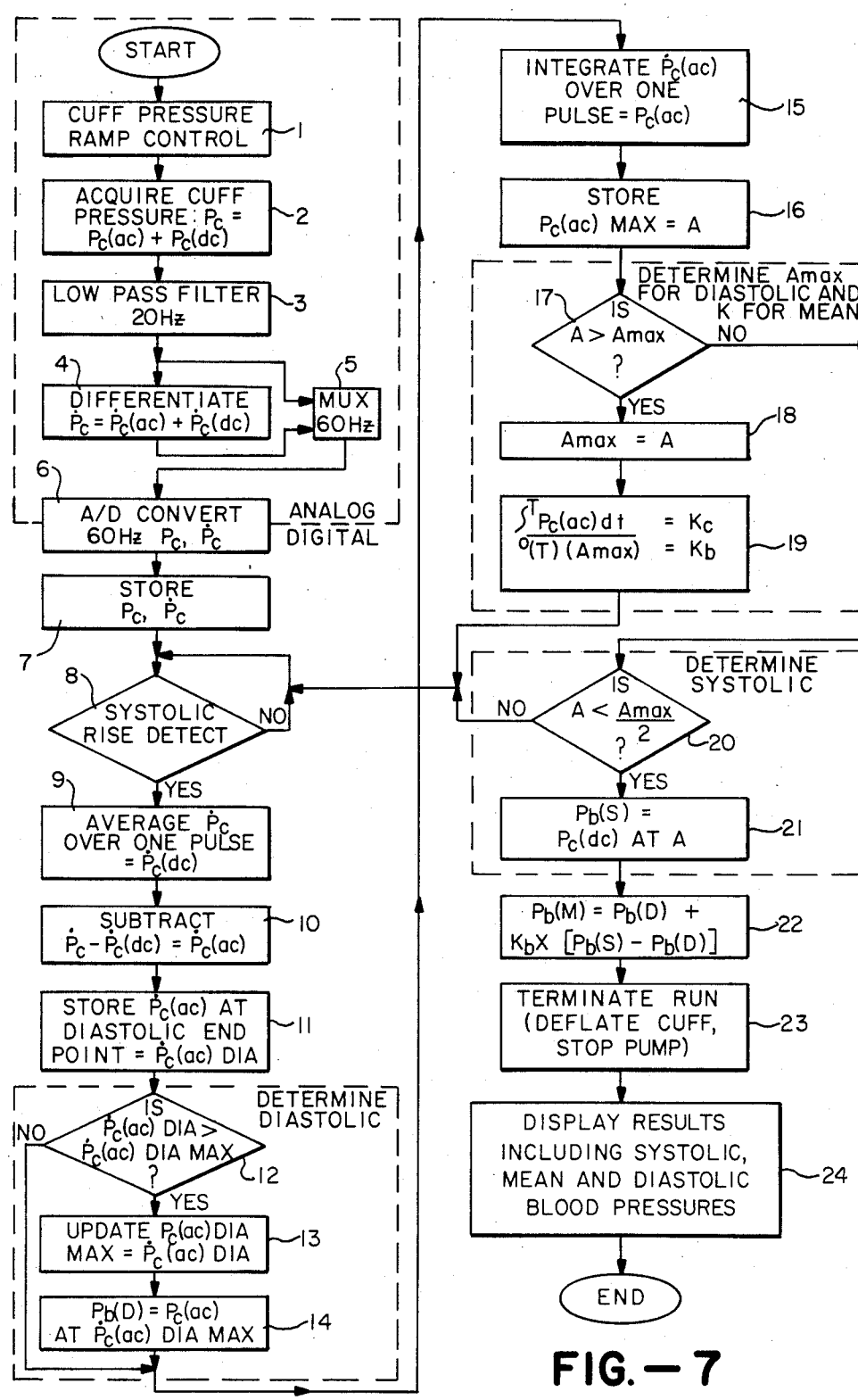
FIG.—7

TECHNIQUE FOR OBTAINING THE MEAN BLOOD PRESSURE CONSTANT FOR AN INDIVIDUAL'S BLOOD PRESSURE

This is a continuation of application Ser. No. 868,252 filed May 28, 1986, now abandoned.

BACKGROUND OF THE INVENTION

The present invention relates generally to blood pressure evaluation procedures and more particularly to a non-invasive, oscillometric technique for determining certain information associated with blood pressure, specifically its mean pressure and blood pressure constant.

In applicant's copending patent application Ser. No. 684,592, filed Dec. 21, 1984, now abandoned incorporated herein by reference, there was described a non-invasive, oscillometric technique for generating a waveform (FIG. 7 of the copending application) which approximates the actual blood pressure waveform of a given mammal (hereinafter referred to as the patient or subject). The copending application also described non-invasive techniques for obtaining the diastolic and systolic pressures of a patient. The copending application further described a technique for utilizing this information, that is, the approximated blood pressure waveform, and the diastolic and systolic pressures, to approximate the patient's mean blood pressure and blood pressure constant. More specifically, as discussed in detail in the copending application, the mean pressure $P_b(M)$ of the approximated blood pressure waveform is equal to the diastolic blood pressure $P_b(D)$ of the subject plus a particular fraction $K_b$ (the blood pressure constant) of the difference between the patient's systolic blood pressure $P_b(S)$ and his diastolic blood pressure $P_b(D)$. Equation 1 below shows this.

$$P_b(M) = P_b(D) + K_b(P_b(S) - P_b(D)) \qquad 1$$

Note that the mean pressure $P_b(M)$ can be calculated by integrating the waveform (its pressure amplitude $P_b$) over its period T (the duration of the waveform) so that:

$$P_b(M) = \frac{\int_0^T P_b\,dt}{T} \qquad 2$$

$$K_b = \frac{P_b(M) - P_b(D)}{P_b(S) - P_b(D)} = \frac{\int_0^T P_b\,dt - P_b(D)}{P_b(S) - P_b(D)} \qquad 3$$

We can also define all of the above in terms of the equivalents analogous quantities found from our measurement of the non-invasive cuff pulses.

Thus we have the analogous minimum and maximum cuff pulse pressures $P_c(D)$ and $P_c(S)$ respectively and the analogous cuff means pressure and cuff pressure constant $P_c(M)$ and $K_c$. The equations analogous to 1, 2 and 3 above are:

$$P_c(M) = P_c(D) + K_c(P_c(S) - P_c(M)) \qquad 4$$

$$P_b(M) = \frac{\int_0^T P_c\,dt}{T} \qquad 5$$

$$K_c = \frac{P_c(M) - P_c(D)}{P_c(S) - P_c(D)} \qquad 6$$

With the above equations in mind, the mean blood pressure value $P_b(M)$ and the blood pressure constant $K_b$ can be determined non-invasively by first generating again, non-invasively, a cuff waveform which approximates the subject's actual blood pressure waveform and determining the subject's diastolic and systolic cuff and blood pressure, as described in the copending application.

SUMMARY OF THE INVENTION

While the procedure just discussed and described in detail in applicant's copending application is an accurate way to determine a subject's mean blood pressure and blood pressure constant without resorting to invasive techniques, an object of the present invention is to provide even less complicated and just as reliable a technique to obtain the same information without having to generate an approximated blood pressure waveform. As will be seen hereinafter, this is accomplished in accordance with the present invention by first generating a series of cuff pulses from the actual blood pressure pulses of the subject. The patient's mean blood pressure is determined directly from a particular one or small group of these cuff pulses, including specifically the cuff pulse having the maximum peak to peak amplitude by integrating this latter cuff pulse (and each of the others if they are selected) and solving for the equation:

$$P_c(M) = \frac{\int_0^T P_c\,dt}{T} \qquad 7$$

Again where $P_c(M)$ is the mean value, T is the duration in time of the cuff pulse and $P_c$ is the cuff pulses amplitude in pressure. Where more than one cuff pulse is selected, the mean value of each is obtained and they are averaged to provide an average mean value. The patient's blood pressure constant $K_b$ can then be obtained by determining the patient's diastolic and systolic cuff pressure points $P_c(D)$ and $P_c(S)$, respectively and solving the equation $$K_b = K_c = \frac{P_c(M) - P_c(D)}{P_c(S) - P_c(D)} \qquad 8$$

The important point in the above is that for only one selected cuff pulse, or perhaps for a few centered around the selected cuff pulse, can we assume the equivalent in 8 above that $$K_b = K_c \qquad 9$$

In simple terms, the K values of the cuff pressure pulses and of the blood pressure pulses are closely the same only for the particular cuff pressure pulse which is the largest of a complete run. We can therefore determine the K value of this particular cuff pulse and hence the mean blood pressure.

The procedure just described requires only that the subject's diastolic and systolic blood and cuff pressure points be determined and that a series of cuff pulses be generated in order to then calculate a reliable approximation of the patient's blood pressure constant and then the mean blood pressure. This is to be contrasted with the technique described in the above recited pending LINK application which requires that an approximated blood pressure waveform be generated before the patient's mean blood pressure and blood pressure constant can be determined. The present technique is less complicated and believed to be just as accurate.

BRIEF DESCRIPTION OF THE DRAWINGS

This technique will be described in more detail hereinafter in conjunction with the drawings wherein:

FIG. 1 diagrammatically illustrates a full series of cuff pulses from a cuff pressure of 160 torr to a cuff pressure of 0;

FIG. 2 is an enlarged diagrammatic illustration of one of the cuff pulses illustrated in FIG. 1, specifically the cuff pulse having the maximum peak to peak amplitude;

FIG. 3 diagrammatically illustrates a transformation or arterial curve corresponding to the one shown in FIG. 2 of the above recited copending application and specifically illustrates the relationship between this curve and actual blood pressure pulse of the subject and the cuff pulse illustrated in FIG. 2;

FIG. 4 is a diagrammatic illustration of an actual blood pressure pulse of the subject along with a superimposed corresponding cuff pulse;

FIG. 5 is a functional illustration of an arrangement for approximating the mean value $P_b(M)$ and blood pressure constant $K_b$ of the subject in accordance with the present invention;

FIG. 7 is a flow diagram illustrating the way in which the computer forming part of the actual embodiment of FIG. 6 is controlled to carry out the present invention.

DETAILED DESCRIPTION

Figure 6:
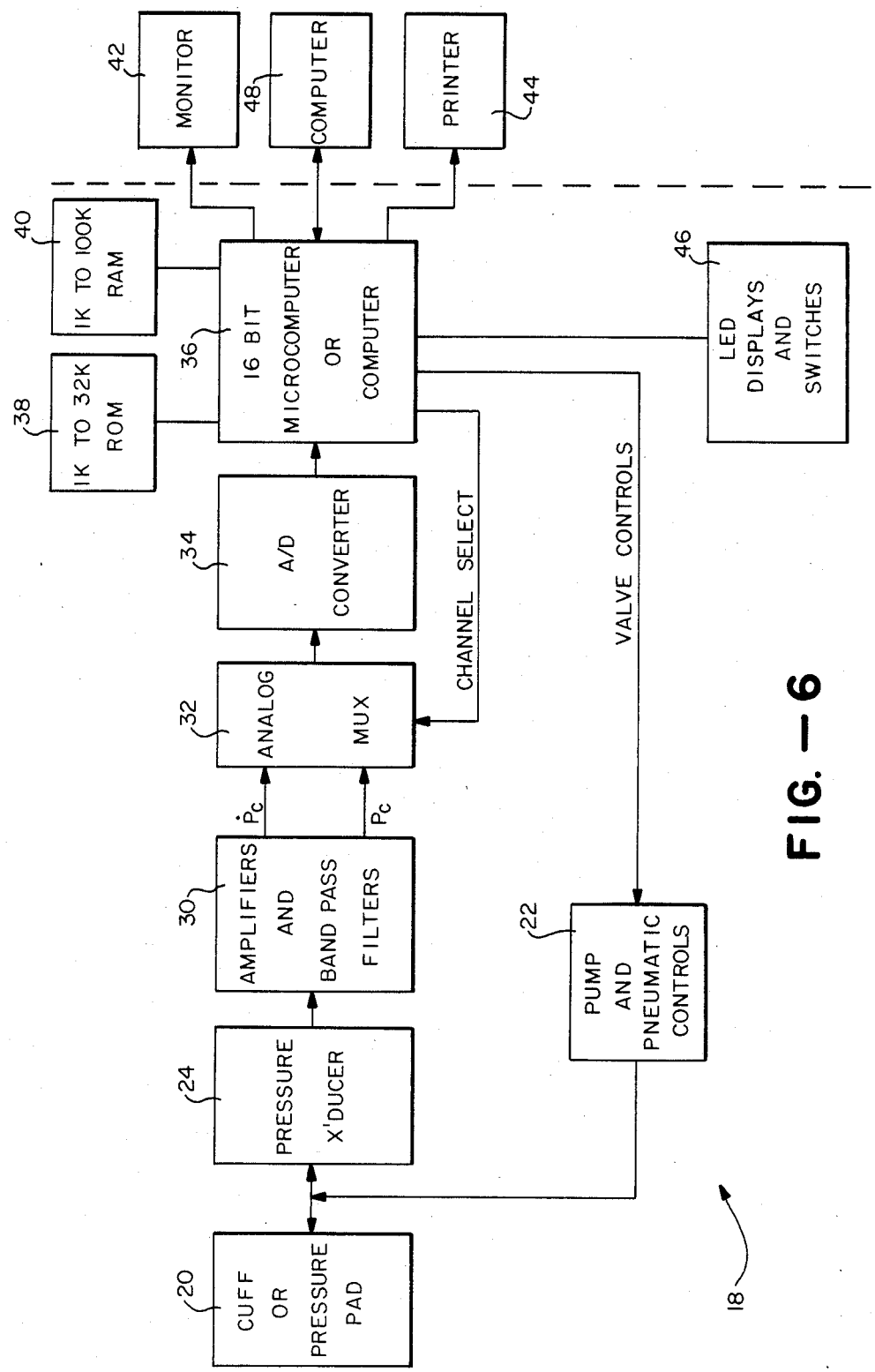
FIG. 6 illustrates a block diagram of an actual working embodiment of the apparatus of FIG. 5.

Turning now to the drawings, a series of cuff pressure waveforms (hereinafter referred to as cuff pulses $P_c(ac)$) $10a$ through $20q$ are illustrated. These pulses are generated in a known manner by placing a blood pressure cuff and other suitable blood pressure cuff means around or adjacent the particular subject or patient being evaluated. Thereafter, the blood pressure cuff or cuff means (hereinafter merely referred to as a blood pressure cuff) is pressurized to a number of different pressure levels $P_c(dc)$ or merely $P_c$ from a pressure of zero to a pressure of 160 torr or any other pressure which is preferably higher than the anticipated systolic pressure of the subject. At each of these pressure levels, the cuff combines with the actual blood pressure pulse of the subject to generate the cuff pulses illustrated. Thus, the cuff pressure $P_c(dc)$ of 160 torr results in a cuff pulse $10a$, a cuff pressure of 150 torr results in a cuff pulse $10b$, and so on. Note that the peak to peak amplitude of these various cuff pulses vary with cuff pressure. This is an important aspect of the present invention, as will be seen hereinafter. Therefore, the actual peak to peak values of these cuff pulses have been provided in FIG. 1.

As indicated above, applicant provided in his copending application Ser. No. 684,592, now abandoned a technique for obtaining the mean blood pressure $P_b(M)$ and the blood pressure constant $K_b$ of a particular subject by generating an approximated blood pressure waveform and using this waveform in combination with the subject's diastolic and systolic blood pressures. Since then, applicant has discovered that he can obtain this same information just as accurately without resorting to an approximated blood pressure waveform. Rather he can obtain the same information directly from a particularly selected cuff pulse in combination with the subject's diastolic and systolic pressures. The specific cuff pulse which makes this possible is the one having a maximum peak to peak amplitude, for example the cuff pulse $10h$ forming part of the group illustrated in FIG. 1. Note that this latter cuff pulse which is illustrated by itself in FIG. 2 has a peak to peak amplitude of 2.9 as compared to the next largest cuff pulse $10g$ which has a peak to peak amplitude of 2.8 and the third largest one $10i$ which has a peak to peak amplitude of 2.5. These values are in centimeters and are actually taken from an oscilloscope readout but can be provided in many known ways electronically. In any event, once the maximum cuff pulse is selected, it can be readily integrated in the same manner as the approximated blood pressure waveform, as described in applicant's above recited copending application. Specifically, applicant has discovered that the mean blood pressure of a subject can be accurately and reliably approximated by integrating cuff pulse $10h$ directly rather than having to generate an approximated blood pressure waveform. Thus, the blood pressure constant $K_b$ can be determined by integrating cuff pulse $10h$ and solving for the equation $$P_c(M) = \frac{\int_0^T P_c dt}{T} \quad 10$$

$$K_b = K_c = \frac{P_c(M) - P_c(D)}{P_c(S) - P_c(D)}$$

where $P_c(M)$ is the mean value, T is the duration in time of cuff pulse $10h$ and $P_c$ is the cuff pulse pressure amplitude.

In equation 10 the values $P_c(D)$ and $P_c(S)$ are simply read off the graph of the maximal pulse #$10h$.

It is important to note that not just any cuff pulse when integrated in the manner just recited will provide the subject's blood pressure constant $K_b$. For example, integrating the waveform $10e$ will not provide for a reliable approximation nor will the cuff pulse $10m$. The reasons for this will be discussed below. For the moment, it suffices to say that the cuff pulse used must be the one having a maximum peak to peak amplitude or a group of cuff pulses close to and including the one having a maximum peak to peak amplitude may be selected, integrated, and averaged out. Specifically, as a second embodiment, the present invention contemplates selecting, for example, the maximum cuff pulse $10h$ and the cuff pulses $10g$ and $10i$. Each would be integrated in the manner discussed above so as to determine the subject's $K_c$ for that cuff pulse and then these three mean pressures would be averaged to provide a single averaged mean $K_c = K_b$. Whether plural cuff pulses are used or a single maximum cuff pulse, once the subject's mean blood pressure constant is determined, his mean blood pressure can be readily calculated by determining his diastolic and systolic pressures $P_b(D)$ and $P_b(S)$, respectively and solving for equation 1 above.

There are a number of different ways to determine the diastolic pressures of a subject, non-invasively, as outlined in applicant's above recited copending application. As a result, a discussion of these various techniques will not be provided here.

Having described how the subjects mean blood pressure $P_b(M)$ and blood pressure constant $K_b$ are approximated directly from a particular one or group of his cuff pulses in combination with his diastolic and systolic pressures, attention is now directed to a discussion of why this is possible. Therefore, attention is directed specifically to FIG. 3 in conjunction with the discussion in applicant's above recited copending application of FIGS. 2 and 3 there. FIG. 3 in the present application illustrates the transformation curve 12 and an actual blood pressure pulse 16 of the subject superimposed on curve 12. For purposes of explanation, the actual blood pressure pulse 16 is shown triangular in configuration rather than as it actually exists. More specifically, both the systolic rise $S_r$ and the diastolic decline $D_d$ are shown perfectly straight which is not actually the case, as will be seen hereinafter with respect to FIG. 4. However, again for purposes of explanation, they will be shown in the manner illustrated in FIG. 3. It should also be noted that the actual blood pressure pulse 16 in FIG. 3 is shown along the transformation curve corresponding to a cuff pressure which results in a maximum cuff pulse. This is discussed in detail in applicant's above recited copending application and particularly with respect to FIG. 3 of that application. As a result, half of the actual blood pressure pulse lies on the concave up side of the transformation curve while the other half lies on its concave down side. Thus, of the section of transformation curve 12 which acts on the actual blood pressure cuff to provide a corresponding cuff pulse, one half lies on the concave up side of the curve and one half lies on its concave down side. These two halves are generally indicated in FIG. 3 at 12a and 12b. Note that the section 12a is slightly concave down while section 12b is slightly concave up. This is important to keep in mind during the discussion to follow.

Still referring to FIG. 3, a cuff pulse which for purposes of convenience will be referred to by the reference numeral 10h' is shown superimposed on transformation curve 12 along with blood pressure pulse 16. Cuff pulse 10h' results from the interaction of cuff pulse 16 and the blood pressure cuff at a particular cuff pressure which produces a maximum cuff pulse. In the case of FIG. 1, the cuff pressure is 90 torr. For purposes of clarity, the diastolic decline of cuff pulse 10h' is shown in two ways; first by means of a straight dotted line and also by means of a solid curved line. Theoretically, if sections 12a and 12b of transformation curve 12 were entirely straight then the diastolic decline of the cuff pulse 10h' would be straight since the diastolic decline of the blood pressure pulse is also assumed to be straight or "true" with respect to the blood pressure pulse. However, as indicated above, section 12a of the transformation curve is slightly concave down and section 12b is slightly concave up. Therefore, the diastolic decline of cuff pulse 10h' includes corresponding concave down and concave up sections and thus is "distorted" with respect to the blood pressure pulse. Since half of the diastolic decline of blood pressure pulse 16 is located on the concave down side of the transformation curve and half is located on the concave up side, half of the diastolic decline of distorted cuff pulse 10h' is concave down and one half is concave up. As a result, as best illustrated in FIG. 3, the surface area under the solid line or distorted diastolic decline of cuff pulse 10h' is equal to the surface area under an ideal or true diastolic decline of the cuff pulse, that is, one having a straight diastolic decline. In other words, even though the ideal cuff pulse is distorted by the convex/concave nature of the transformation curve, the particular cuff pulse associated with the blood pressure pulse 16, that is, the cuff pulse having a maximum peak to peak amplitude has the same integrated value across its entire extent as does the actual blood pressure pulse. This is best exemplified in FIG. 4 which shows an actual blood pressure pulse 16' which corresponds to the diagrammatically illustrated pulse 16, in solid lines. The curve represented by the dotted lines is a corresponding, actual cuff pulse 10h. Note that while the actual cuff pulse 10h has a different shape than the actual blood pressure pulse 16', both have approximately the same surface area and therefore the same mean value.

Turning now to FIG. 5, a non-invasive apparatus 18 is shown for carrying out the procedure described immediately above, that is, for approximating the subjects mean blood pressure $P_b(M)$ and blood pressure constant $K_b$ in accordance with the present invention. This apparatus includes a blood pressure cuff or other suitable cuff means 20 positionable around or adjacent a specific artery of the subject in the normal operating manner and means generally indicated at 22 for maintaining the cuff at different pressure levels from zero pressure to, for example 160 torr. Cuff 20 must be pressurized to a sufficiently high level to insure that the cuff pulse having maximum peak to peak amplitude is generated. However, as a practical matter, the cuff should be pressurized to a level higher than the anticipated systolic pressure of the subject since these same cuff pulses can be utilized to determine the subject's diastolic and systolic pressures in accordance with procedures described in applicant's previously recited copending application. In any event, the resultant cuff pulses are monitored by transducer 24. Suitable and readily providable electronic means 26 to be discussed in more detail with respect to FIG. 6 serves to receive these pulses and selects the one having the maximum peak to peak amplitude or a group of ones having peak to peak amplitudes. The electronic means then integrates the cuff pulse or pulses selected in order to provide the approximated mean blood pressure of the subject in the manner described above. This value can then be used to calculate the subject's blood pressure constant $K_b$. An oscilloscope or other suitable monitoring means 28 can then be utilized to read out or record these values.

Having described apparatus 18 generally, attention is now directed to FIG. 6 which illustrates the apparatus by means of a block diagram. As illustrated there, the apparatus includes the previously recited blood pressure cuff or cuff means 20 which can also be, for example, a pressure pad positioned at an appropriate location around (in the case of a cuff) or adjacent (in the case of a pad) a suitable artery of the subject. In this latter regard, as indicated previously, it is to be understood that either a cuff, or a pad, a bladder or any other suitable pressurizing means may be utilized, although for purposes of clarity, only a cuff has been recited. Also, the term cuff pulse or cuff pressure used herein refers to pressure and pulses from any of these means.

Still referring to FIG. 6, overall apparatus 18 is shown including a pump and suitable pneumatic controls serving as previously recited means 22 for pressurizing the cuff (or pad) to the previously recited different pressure levels. Pressure transducer 24 is shown coupling the cuff or pressure pad to a combination of amplifiers and band pass filters for producing cuff pulses such as the ones illustrated in FIG. 1.

An analog MUX, an A/D converter and a 16-bit microcomputer or any or suitable computer means indicated generally at 32, 34 and 36 respectively are connected in the manner illustrated in FIG. 6, cooperate to provide means for digitizing the analog cuff pressures, i.e., the cuff pressures $P_c(dc)$ and the cuff pulses $P_c(ac)$. The microcomputer or computer generally is controlled by a suitable program stored in ROM 38 in order to carry out the necessary steps of overall apparatus 18. This program may vary in length from for example 1k bytes to as much as 32k bytes, depending upon accuracy and other factors. The digitized value of cuff pulses $P_c(ac)$ and cuff pressures $P_c(dc)$ and other necessary information, e.g., the transformation curve 12, are stored by computer 36 in a RAM 40. The computer determines the diastolic and systolic pressures of the subject and the subject's mean blood pressure and blood pressure constant and outputs the results to a monitor 42, a printer 44, an LED display 46 and/or perhaps to another computer 48. It can be seen that the RAM memory must be sufficiently large to store the various cuff pulses as well as the transformation curves described above.

As indicated immediately above ROM 38 forming part of overall apparatus 18 is controlled by a suitable program in order to carry out the necessary steps of overall apparatus 18. Turning now to FIG. 7, there is shown a flow diagram corresponding to the procedure described previously with respect to FIGS. 1–5 and incorporating the various steps carried out by the computer forming part of the block diagram illustrated in FIG. 6. Before proceeding with a description of this flow diagram, it should be noted that the term "$\dot{P}c$" therein refers to the combination of cuff applied pressure $Pc(dc)$ and cuff pulses $Pc(ac)$ and that the $\dot{P}c$ refers to the derivative of $Pc$ and therefor the sum of the derivative of the cuff applied pressure $\dot{P}c(dc)$ plus the derivative of the cuff pulses $\dot{P}c(ac)$. It should be further noted that the derivative of the cuff pressure $\dot{P}c(dc)$ corresponds to the pressure ramp characteristic resulting from the way in which the blood pressure cuff is pressurized. More specifically, as each cuff pulse $Pc(ac)$ is generated at a given cuff pressure $Pc(dc)$ it is done at continuously greater or lesser cuff pressures which form a continuously upwardly extending or downwardly extending ramp.

As will be seen below, the first ten steps (boxes) and box 19 in the flow diagram of FIG. 7 serve to receive physical cuff pressures from the cuff and these cuff pressures are converted to electrical analog signals and then digital signals and eventually the ramp component or gradient of the overall signal which is signal $Pc$ is eliminated so as to provide the cuff pulses $Pc(ac)$ by themselves on a horizontal axis rather than along a ramp gradient. At the same time, the overall signal $Pc$ and the cuff pulses $Pc(ac)$ are differentiated.

Referring now specifically to the flow diagram, step one begins after the start button is depressed and corresponds to pressurizing the cuff at different upwardly ramping or downwardly ramping cuff pressures $Pc(dc)$. In step two the transducer forming part of the overall system receives the cuff pressures and converts them to analog signals which are filtered for 60 hz and noise (step three). These signals $Pc$ are then differentiated by box four and the differentiated components $\dot{P}c(ac)$ and $\dot{P}c(dc)$ are alternately fed to an analog/digital converter (box six) by means of the multiplexer corresponding to box five. Both $Pc$ and $\dot{P}c$ are stored in RAM as represented by box seven. As this is done, the system as represented by box eight continuously searches for the beginning of the cuff pulse by specifically looking for the beginning of its systolic rise. When that is found, $\dot{P}c$ is averaged (integrated) over a full pulse and therefore corresponds to $\dot{P}c(dc)$ or the ramp gradient. Finally, as indicated in box ten, $\dot{P}c(dc)$ is subtracted from $\dot{P}c$ leaving $\dot{P}c(ac)$ which is the differential without the ramp gradient. Box fourteen integrates $\dot{P}c(ac)$ to provide the cuff pulses by themselves, that is, without the ramp gradient. These separated cuff pulses and both $Pc$ and $\dot{P}c$ are stored in RAM.

Continuing on with the flow diagram, step 11 stores the $\dot{P}(ac)$ at the diastolic end point and boxes 12–14 determine the diastolic pressure of the subject pursuant to U.S. Pat. No. 3,903,872. Box 16 stores the maximum cuff pulse and the boxes 17–19 integrate the maximum cuff pulse while boxes 20 and 21 determine the systolic pressure. Box 22 determines the mean blood pressure and box 23 terminates the run.

From the foregoing, it can be seen that various cuff pulses $Pc(ac)$ can be obtained including specifically a cuff pulse having a maximum amplitude. The procedure can then be terminated by, for example, determining that the cuff pulses have been produced at cuff pressures exceeding the systolic pressure. The maximum cuff pulses can be integrated in order to determine the K value and diastolic and systolic pressures can be determined, as indicated in the flow diagram and from this information can be obtained the mean blood pressure. All of this information can then be read out.

What is claimed is:

1. A non-invasive method of approximating at least one specific parameter associated with the actual blood pressure pulse in a particular artery of a given subject, which parameter is the mean blood pressure $P_{(b)}M$ of said subject, said method comprising the steps of:
    (a) by non-invasive means, generating a particular cuff pulse from said actual blood pressure pulse by
        (i) placing blood pressure cuff means adjacent said particular artery of said subject, and
        (ii) pressurizing said cuff means to a number of different pressure levels including a specific level and generating from said different pressure levels cuff pulses having peak to peak amplitude values corresponding to and dependent on said different pressure levels, said specific pressure level being one which corresponds to the cuff pulse having a maximum peak to peak amplitude value, said last-mentioned cuff pulse serving as said particular cuff pulse;
    (b) determining the mean value under said particular cuff pulse by integrating said particular cuff pulse and solving for the equations $$P_c(M) = \frac{\int_0^T P_c dt}{T}$$

$$K_b = K_c = \frac{P_c(M) - P_c(D)}{P_c(S) - P_c(D)}$$

where $P_c(M)$ is said mean value, T is the duration in time of said cuff pulse, $P_c$ is the cuff pulse pressure amplitude, $P_c(D)$ and $P_c(S)$ are the minimum and maximum pressures, respectively, of the cuff pulse, $K_b$ is the subject's blood pressure constant and $K_c$ is the cuff pressure constant of said cuff pulse;

(c) by non-invasive means, determining the diastolic and systolic pressure points $P_b(D)$ and $P_b(S)$, respectively, of said actual blood pressure pulse; and (d) using the blood pressure constant $K_b$ of said subject, and said diastolic and systolic pressure points $P_b(D)$ and $P_b(S)$, calculating the subject's mean blood pressure value $P_b(M)$ by solving the equation $$P_b(M) = P_b(D) + K_b(P_b(S) - P_b(D)).$$

2. A non-invasive method of approximating at least one specific parameter associated with the actual blood pressure pulse in a particular artery of a given subject, which parameter is the mean blood pressure $P_{(b)}M$ of said subject, said method comprising the steps of:

(a) by non-invasive means, generating a group of particular cuff pulses from said actual blood pressure pulse by
 (i) placing blood pressure cuff means adjacent said particular artery of said subject, and
 (ii) pressurizing said cuff means to a number of different pressure levels including specific levels and generating from said different pressure levels cuff pulses having peak to peak amplitude values corresponding to and dependent on said different pressure levels, said specific pressure levels being ones which correspond to cuff pulses having maximum peak to peak amplitude values as compared to the rest of the cuff pulses, said last-mentioned cuff pulses serving as said particular cuff pulses;

(b) determining the mean value under each of said particular cuff pulses by integrating each of said particular cuff pulses and solving for the equations $$P_c(M) = \frac{\int_0^T P_c dt}{T}$$

$$K_b = K_c = \frac{P_c(M) - P_c(D)}{P_c(S) - P_c(D)}$$

where $P_c(M)$ is said mean value, T is the duration in time of said cuff pulse, $P_c$ is the cuff pulse pressure amplitude, $P_c(D)$ and $P_c(S)$ are the minimum and maximum pressures, respectively, of the cuff pulse, $K_b$ is the subject's blood pressure constant and $K_c$ is the cuff pressure constant of said cuff pulse;

(c) averaging the mean values $P_c(M)$ for all of said particular cuff pulses to provide an average mean value;

(d) by non-invasive means, determining the diastolic and systolic pressure points $P_b(D)$ and $P_b(S)$, respectively, of said actual blood pressure pulse; and (e) using the blood pressure constant $K_b$ of said subject, and said diastolic and systolic pressure points $P_b(D)$ and $P_b(S)$, calculating the subject's mean blood pressure value $P_b(M)$ by solving the equation $$P_b(M) = P_b(D) + K_b(P_b(S) - P_b(D)).$$

3. A method according to claim 2 wherein said particular cuff pulses consist of three cuff pulses, one having a maximum peak to peak amplitude level and the other two having peak to peak amplitudes which have the second and third largest peak to peak levels.

4. A non-invasive apparatus for approximating at least one specific parameter associated with the actual blood pressure pulse in a particular artery of a given subject, which parameter is the mean blood pressure $P_{(b)}M$ of said subject, said apparatus comprising:

(a) non-invasive means for generating a particular cuff pulse from said actual blood pressure pulse including
 (i) blood pressure cuff means positionable adjacent said particular artery of said subject, and
 (ii) means for pressurizing said cuff means to a number of different pressure levels including a specific level and generating from said different pressure levels cuff pulses having peak to peak amplitude values corresponding to and dependent on said different pressure levels, said specific pressure level being one which corresponds to the cuff pulse having a maximum peak to peak amplitude value, said last-mentioned cuff pulse serving as said particular cuff pulse;

(b) means for determining the mean value under said cuff pulse by integrating said cuff pulse and solving for the equations $$P_c(M) = \frac{\int_0^T P_c dt}{T}$$

$$K_b = K_c = \frac{P_c(M) - P_c(D)}{P_c(S) - P_c(D)}$$

where $P_c(M)$ is said mean value, T is the duration in time of said cuff pulse, $P_c$ is the cuff pulse pressure amplitude, $P_c(D)$ and $P_c(S)$ are the minimum and maximum pressures, respectively, of the cuff pulse, $K_b$ is the subject's blood pressure constant and $K_c$ is the cuff pressure constant of said cuff pulse;

(c) non-invasive means for determining the diastolic and systolic pressure points $P_b(D)$ and $P_b(S)$, respectively, of said actual blood pressure pulse; and (d) means using the blood pressure constant $K_b$ of said subject, and said diastolic and systolic pressure points $P_b(D)$ and $P_b(S)$, for calculating the subject's mean blood pressure value $P_b(M)$ by solving the equation $$P_b(M) = P_b(D) + K_b(P_b(S) - P_b(D)).$$

5. A non-invasive apparatus for approximating at least one specific parameter associated with the actual blood pressure pulse in a particular artery of a given subject, which parameter is the mean blood pressure $P_{(b)}M$ of said subject, said apparatus comprising:

(a) non-invasive means for generating a group of particular cuff pulses from said actual blood pressure pulse by
 (i) blood pressure cuff means positionable adjacent said particular artery of said subject, and
 (ii) means for pressurizing said cuff means to a number of different pressure levels including specific levels and generating from said different pressure levels cuff pulses having peak to peak amplitude values corresponding to and dependent on said different pressure levels, said specific pressure levels being ones which correspond to cuff pulses having maximum peak to peak amplitude values as compared to the rest of the cuff pulses, said last-mentioned cuff pulses serving as said particular cuff pulses;
(b) means for determining the mean value under each of said particular cuff pulses by integrating each of said particular cuff pulses and solving for the equations $$P_c(M) = \frac{\int_0^T P_c dt}{T}$$

$$K_b = K_c = \frac{P_c(M) - P_c(D)}{P_c(S) - P_c(D)}$$

where $P_c(M)$ is said mean value, T is the duration in time of said cuff pulse, $P_c$ is the cuff pulse pressure amplitude, $P_c(D)$ and $P_c(S)$ are the minimum and maximum pressures, respectively, of the cuff pulse, $K_b$ is the subject's blood pressure constant and $K_c$ is the cuff pressure constant of said cuff pulse;
(c) averaging the mean values $P_c(M)$ for all of said particular cuff pulses to provide an average mean value;
(d) non-invasive means for determining the diastolic and systolic pressure points $P_b(D)$ and $P_b(S)$, respectively, of said actual blood pressure pulse; and
(e) means using the blood pressure constant $K_b$ of said subject, and said diastolic and systolic pressure points $P_b(D)$ and $P_b(S)$, for calculating the subject's mean blood pressure value $P_b(M)$ by solving the equation $$P_b(M) = P_b(D) + K_b(P_b(S) - P_b(D)).$$

6. An apparatus according to claim 5 wherein said particular cuff pulses consist of three cuff pulses, one having a maximum peak to peak amplitude level and the other two having peak to peak amplitudes which have the second and third largest peak to peak levels.

7. A non-invasive method of approximating at least one specific parameter associated with the actual blood pressure pulse in a particular artery of a given subject, which parameter is the mean blood pressure of said subject, said method comprising the steps of:
(a) by non-invasive means, generating a particular cuff pulse from said actual blood pressure pulse by
 (i) placing blood pressure cuff means adjacent said particular artery of said subject, and
 (ii) pressurizing said cuff means to a number of different pressure levels including a specific level and generating from said different pressure levels cuff pulses having peak to peak amplitude values corresponding to and dependent on said different pressure levels, said specific pressure level being one which corresponds to the cuff pulse having a maximum peak to peak amplitude value, said last-mentioned cuff pulse serving as said particular cuff pulse;
(b) determining the mean value under said particular cuff pulse and the minimum and maximum pressures of said particular cuff pulse;
(c) by non-invasive means, determining the diastolic and systolic pressure points, respectively, of said actual blood pressure pulse; and
(d) using said mean value under said cuff pulse, its minimum and maximum pressures and the diastolic and systolic pressure points of said actual blood pressure pulse, deriving the mean blood pressure of said subject.

8. A non-invasive apparatus for approximating at least one specific parameter associated with the actual blood pressure pulse in a particular artery of a given subject, which parameter is the mean blood pressure of said subject, said apparatus comprising:
(a) non-invasive means for generating a particular cuff pulse from said actual blood pressure pulse including
 (i) blood pressure cuff means positionable adjacent said particular artery of said subject, and
 (ii) means for pressurizing said cuff means to a number of different pressure levels including a specific level and generating from said different pressure levels cuff pulses having peak to peak amplitude values corresponding to and dependent on said different pressure levels, said specific pressure level being one which corresponds to the cuff pulse having a maximum peak to peak amplitude value, said last-mentioned cuff pulse serving as said particular cuff pulse;
(b) means for determining the mean value under said particular cuff pulse and the minimum and maximum pressures of said particular cuff pulse;
(c) non-invasive means for determining the diastolic and systolic pressure points, respectively, of said actual blood pressure pulse; and
(d) means using said mean value under said cuff pulse, its minimum and maximum pressures and the diastolic and systolic pressure points of said actual blood pressure pulse for deriving the mean blood pressure of said subject.

9. A non-invasive method of approximating at least one specific parameter associated with the actual blood pressure pulse in a particular artery of a given subject, which parameter is the mean blood pressure of said subject, said method comprising the steps of:
(a) by non-invasive means, generating a particular group of cuff pulses from said actual blood pressure pulse by
 (i) placing blood pressure cuff means adjacent said particular artery of said subject, and
 (ii) pressurizing said cuff means to a number of different pressure levels including specific levels and generating from said different pressure levels cuff pulses having peak to peak amplitude values corresponding to and dependent on said different pressure levels, said specific pressure levels being ones which correspond to cuff pulses having maximum peak to peak amplitude value, said last-mentioned cuff pulses serving as said particular cuff pulses;
(b) determining the mean value under each of said particular cuff pulses and the minimum and maximum pressures of said particular cuff pulses;
(c) by non-invasive means, determining the diastolic and systolic pressure points, respectively, of said actual blood pressure pulse; and
(d) using said mean value under each of said cuff pulses, their respective minimum and maximum pressures and the diastolic and systolic pressure points of said actual blood pressure pulse, deriving the mean blood pressure of said subject.

* * * * *